(12) United States Patent
Goettel et al.

(10) Patent No.: US 7,517,367 B2
(45) Date of Patent: Apr. 14, 2009

(54) CATIONIC NAPHTHYLDIAZO DYES AND KERATIN FIBERS-COLORING AGENTS CONTAINING THESE DYES

(75) Inventors: Otto Goettel, Marly (CH); Andre Hayoz, Senedes (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 349 days.

(21) Appl. No.: 10/584,955

(22) PCT Filed: Dec. 13, 2004

(86) PCT No.: PCT/EP2004/014189

§ 371 (c)(1),
(2), (4) Date: Jun. 30, 2006

(87) PCT Pub. No.: WO2005/085362

PCT Pub. Date: Sep. 15, 2005

(65) Prior Publication Data

US 2008/0167453 A1   Jul. 10, 2008

(30) Foreign Application Priority Data

Mar. 6, 2004   (DE) .................. 10 2004 010 999

(51) Int. Cl.
*A61Q 5/10* (2006.01)

(52) U.S. Cl. .............................. 8/405; 8/426; 534/603; 534/604; 534/605; 534/615

(58) Field of Classification Search ........................ None
See application file for complete search history.

(56) References Cited

U.S. PATENT DOCUMENTS

| 4,652,632 A | 3/1987 | Colberg |
| 6,774,242 B1 | 8/2004 | Barth et al. |

FOREIGN PATENT DOCUMENTS

| DE | 2 017 497 | 11/1970 |
| DE | 196 18 595 | 11/1997 |
| EP | 0 159 549 | 10/1985 |
| GB | 1 299 080 | 12/1972 |
| WO | 00/42980 | 7/2000 |
| WO | 00/59883 | 10/2000 |
| WO | 03/022233 | 3/2003 |

OTHER PUBLICATIONS

Gmaj et al., Chemical Abstracts, 71:22903, 1969, Abstract of Polish Patent 54538, Registry No. 23472-92-6.*

* cited by examiner

*Primary Examiner*—Fiona T Powers
(74) *Attorney, Agent, or Firm*—Michael J. Striker

(57) ABSTRACT

Cationic naphthyldiazo dyes of general formula (I)

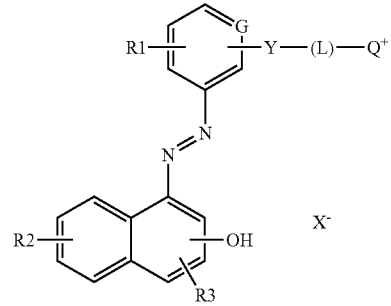

and colorants for keratin fibers containing these dyes.

11 Claims, No Drawings

CATIONIC NAPHTHYLDIAZO DYES AND KERATIN FIBERS-COLORING AGENTS CONTAINING THESE DYES

CROSS-REFERENCE TO RELATED APPLICATIONS

This application claims priority under 35 U.S.C. 119(a)-(d) to German Patent Application DE 102004010999.0, filed 06 Mar. 2004.

BACKGROUND OF THE INVENTION

1. Field of the Invention

The present invention relates to novel direct dyes for preparing non-oxidative colorants for keratin fibers, for example hair, silk or wool.

2. Description of Related Art

The dyeing of human hair is currently subjected to the most varied trends. Whereas previously hair was dyed primarily to cover gray areas for an extended period of time, today an increasing demand exists for integration of the hair color into current fashion and the use of it as an expression of a subject's personality.

As before, two methods are available for the dyeing of hair. One of these methods is oxidative hair dyeing which gives long-lasting dyeing results. The other method consists of non-oxidative tinting which as a rule is more gentle than oxidative dyeing but also less durable. Non-oxidative colorants are advantageous particularly when the customer wants to change the color shades more frequently and at the same time wants to avoid a deterioration of hair quality from frequent exposure to oxidants considering that it is possible to apply non-oxidative ("direct") colorants under very gentle conditions. Because in the case of tints the colorations can be weakened gradually with every hair washing, such colorations normally withstand at the most 10 to 15 hair washings, depending on the product used and the kind of hair. Customers often make use of precisely these properties so that they can later apply new color shades to achieve a different coloring result. For both dyeing methods, the oxidative and the non-oxidative, achieving a high color density on the hair with only minor skin staining is particularly desirable.

Cationic dyes with arylazo groups or heteroarylazo groups as well as anthraquinones and naphthoquinones were found to be particularly well suited for use as tinting agents, the cationic group possibly being delocalized or localized. In this regard we mention, for example, the widely used "Arianor®-Dyes" which not only have good coloring properties but also cause only very minor skin staining. Most "Arianor®-Dyes" are cationic azo dyes, and only the blue dye ("Arianor® Steel-Blue") is a naphthoquinone derivative. A particular problem of these "Arianor®-Dyes" is that the dyes are sometimes washed out at different rates so that, if one or more dyes are washed out more intensely, the color shade can change in an uncontrollable manner.

BRIEF SUMMARY OF THE INVENTION

Surprisingly, we have now found that certain cationic naphthyldiazo dyes are eminently suited for semipermanent dyeing of hair. Moreover, these dyes distinguish themselves by their compatibility with the Arianor® dyes the color range of which they can supplement in ideal fashion. The dyes of the invention also show highly uniform substantivity and unusually high covering power so that for the purpose of achieving special trendy effects they can be used alone or, in cases where natural shades are to be attained, in combination with other dyes of formula (I) or with commercially available direct dyes.

DETAILED DESCRIPTION OF THE INVENTION

The present invention therefore has for an object cationic naphthyldiazo dyes of general formula (I)

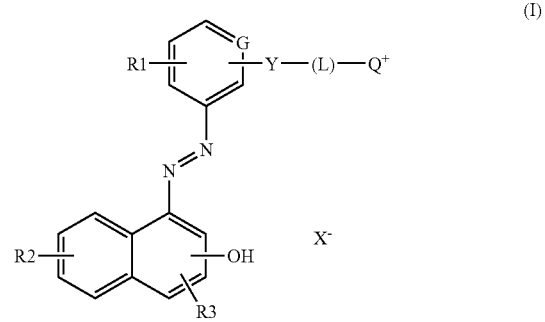

wherein

R1 stands for a hydrogen atom, halogen atom, straight-chain or branched ($C_1$-$C_4$)-alkyl group, straight-chain or branched ($C_1$-$C_4$)-alkoxy group, phenyl group or ($C_2$-$C_4$)-hydroxyalkyl group:

R2 and R3 can be equal or different and independently of each other stand for a hydrogen atom, hydroxyl group, amino group, acetylamino group, ($C_1$-$C_6$)-alkoxy group, ($C_2$-$C_4$)-hydroxyalkoxy group, ($C_3$-$C_6$)-di-or polyhydroxyalkoxy group, —COOR group, —NRR' group or —CONRR' group, wherein R and R' can be equal or different and stand for a hydrogen atom, a straight-chain or branched ($C_1$-$C_6$)-alkyl group or a hydroxyethyl group, or R and R' together with the nitrogen atom to which they are attached form a heterocycle with at least four ring members (preferably four- to six-membered ring) optionally containing other heteroatoms such as oxygen, nitrogen or sulfur and wherein R and R' and the afore-de-scribed heterocycle can be substituted with an alkyl group, alkoxy group, hydro-xyalkyl group or aminoalkyl group;

G stands for a nitrogen atom or a methine group (CH);

Y stands for an oygen atom or an N—($C_1$-$C_4$)-alkyl group;

L represents a bridging group and stands for a straight-chain or branched ($C_1$-$C_{14}$)-alkylene group which optionally can be interrupted by one or more heteroatoms such as oxygen, nitrogen or sulfur, the bridging group optionally being substituted with one or more hydroxyl groups, monohydroxy-($C_2$-$C_6$)-alkyl groups, polyhydroxy-($C_2$-$C_6$)-alkyl groups or ($C_1$-$C_6$)-alkoxy groups;

$Q^+$ stands for a saturated cationic group of formula (II) or an unsaturated cationic group of formulas (III) to (V)

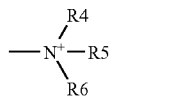

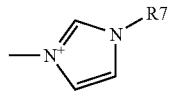

-continued

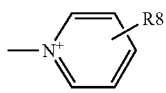

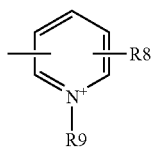

wherein

R4 to R6 can be equal or different and independently of each other stand for a straight-chain or branched $(C_1-C_6)$-alkyl group, $(C_2-C_4)$-hydroxyalkyl group, $(C_3-C_6)$-dihydroxyalkyl group, $(C_3-C_6)$-polyhydroxyalkyl group or $(C_1-C_6)$-alkoxy-$(C_1-C_4)$-alkyl group, wherein two of the R4 to R6 groups together with the nitrogen to which they are attached form a 5-membered to 6-membered heterocycle optionally interrupted by one or more heteroatoms such as an oxygen atom, sulfur atom or nitrogen atom and optionally bearing other substituents, for example a halogen atom, hydroxyl group, amino group, straight-chain or branched $(C_1-C_6)$-alkyl group, $(C_1-C_6)$-alkoxy group, $(C_1-C_6)$-alkoxy-$(C_1-C_4)$-alkyl group, or a hydroxyethyl group;

R7 stands for a straight-chain or branched $(C_1-C_8)$-alkyl group, allyl group, vinyl group, hydroxyethyl group or benzyl group;

R8 stands for a hydrogen atom, straight-chain or branched $(C_1-C_9)$-alkyl group, amino group, di-$(C_1-C_6)$-alkylamino group or pyrrolidino group;

R9 stands for a straight-chain or branched $(C_1-C_8)$-alkyl group, allyl group, vinyl group, hydroxyethyl group, dihydroxypropyl group or benzyl group, and $X^-$ stands for an anion, preferably a chloride, bromide, iodide, alkylsulfate, arylsulfonate, hydrogen sulfate, sulfate, phosphate, acetate or tartrate anion.

Preferred are dyes of formula (I) wherein:

R1 stands for a hydrogen atom, chlorine atom or methyl group;

R2 and R3 are equal or different and independently of each other stand for hydrogen, a hydroxyl group, methoxy group, —NRR' group or —CONRR' group, wherein R and R' can be equal or different and stand for a hydrogen atom, methyl group or hydroxyethyl group or R and R' together with the nitrogen atom to which they are attached form a heterocycle with five or six ring members—for example a pyrrolidino group, 3-hydroxypyrrolidino group, 2-methoxymethylpyrrolidino group, 2,5-bis(methoxymethyl)pyrrolidino group, piperidino group, 3-hydroxypiperidino group, 4-hydroxypiperidino group, 4-methylpiperidino group, 2,3- or 2,6-dimethylpiperidino group, 2-ethylpiperidino group, 4-benzylpiperidino group, morpholino group, N-methylpiperazino group or 1-(2-hydroxyethyl)piperazino group;

G stands for a nitrogen atom or a methine group (CH);

Y stands for oxygen or an N-methyl group;

L stands for a straight-chain $(C_2-C_4)$-bridging group;

$Q^+$ stands for a saturated cationic group of formula (II) or an unsaturated cationic group of formula (III) to (V), the R4 to R6 groups possibly being equal or different and independently of each other denote a straight-chain $(C_1-C_3)$-alkyl group, hydroxyethyl group or methoxyethyl group, or two of the R4 to R6 groups together with the nitrogen atom to which they are attached form a five-membered or six-membered heterocycle, for example a pyrrolidino group, 3-hydroxypyrrolidino group, 2-methoxymethylpyrrolidino group, 2,5-bis(methoxymethyl)pyrrolidino group, piperidino group, 3-hydroxypiperidino group, 4-hydroxypiperidino group, 2-methylpiperidino group, 3-methylpiperidino group, 4-methylpiperidino group, 2,6-dimethylpiperidino group, 2-ethylpiperidino group, 4-benzylpiperidino group, morpholino group, N-methylpiperazino group or 1-(2-hydroxyethyl)piperazino group;

R7 stands for a methyl group or hydroxyethyl group;

R8 stands for a hydrogen atom, methyl group, dimethylamino group or pyrrolidino group;

R9 stands for a methyl group, ethyl group or hydroxyethyl group, and $X^-$ stands for a chloride anion, bromide anion or methylsulfate anion.

Particularly preferred are the following dyes of formula (I):

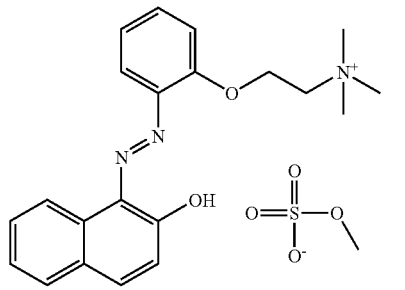

2-{2-[(2-hydroxy-1-naphthyl)diazenyl]phenoxy}-N,N,N-trimethylethanaminium methylsulfate (1)

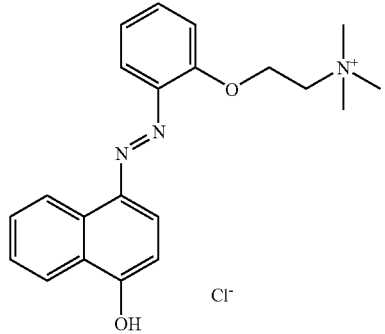

2-{2-[(4-hydroxy-1-naphthyl)diazenyl]phenoxy}-N,N,N-trimethylethanaminium chloride (2)

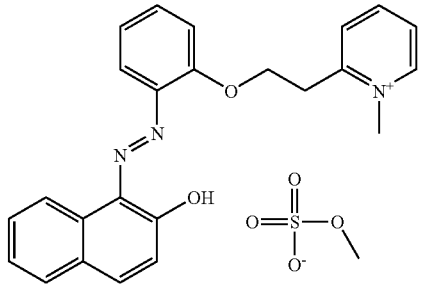

2-(2-{2-[(2-hydroxy-1-naphthyl)diazenyl]phenoxy}ethyl)-1-methylpyridinium methylsulfate (3)

-continued

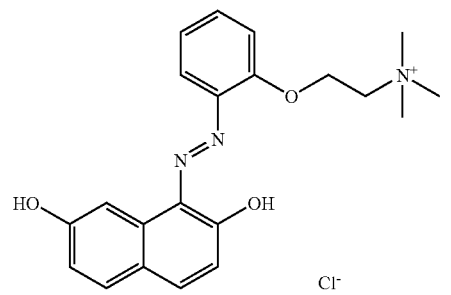

2-{2-[(2,7-dihydroxy-1-naphthyl)diazenyl]phenoxy}-N,N,N-trimethylethanaminium chloride (4)

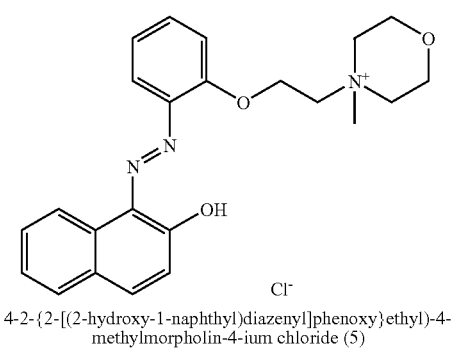

4-2-{2-[(2-hydroxy-1-naphthyl)diazenyl]phenoxy}ethyl)-4-methylmorpholin-4-ium chloride (5)

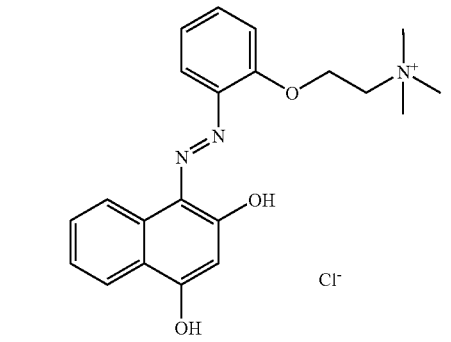

2-({2-[(2,4-dihydroxy-1-naphthalenyl)diazenyl]phenyl}oxy)-N,N,N-trimethylethanaminium chloride (6)

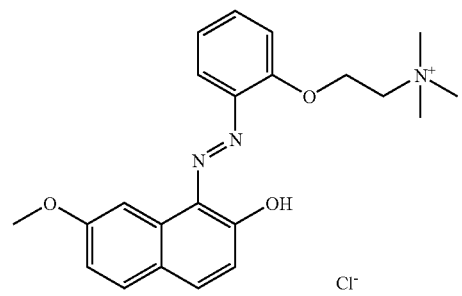

2-[(2-{(2-hydroxy-7-(methoxy)-1-naphthalenyl]diazenyl}phenyl)oxy]-N,N,N-trimethylethanaminium chloride (7)

-continued

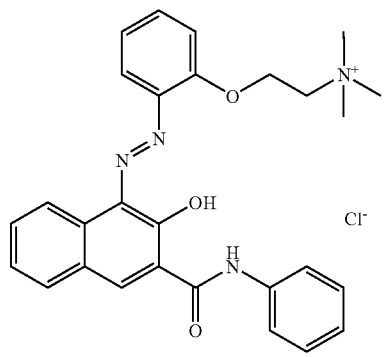

2-{[2-({2-hydroxy-3-[(phenylamino)carbonyl]-1-naphthalenyl}diazenyl)phenyl]-oxy}-N,N,N-trimethylethanaminium chloride (8)

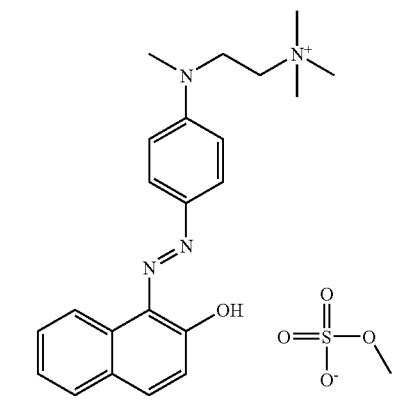

2-[{4-[(2-hydroxy-1-naphthalenyl)diazenyl]phenyl}(methyl)amino]-N,N,N-trimethylethanaminium methylsulfate (9)

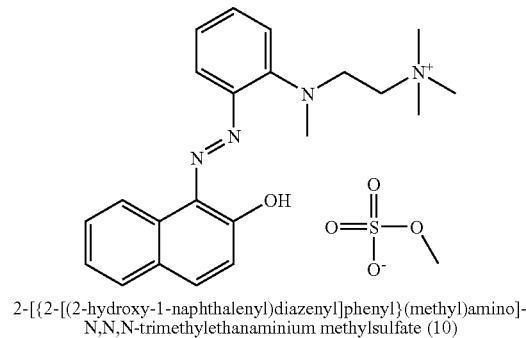

2-[{2-[(2-hydroxy-1-naphthalenyl)diazenyl]phenyl}(methyl)amino]-N,N,N-trimethylethanaminium methylsulfate (10)

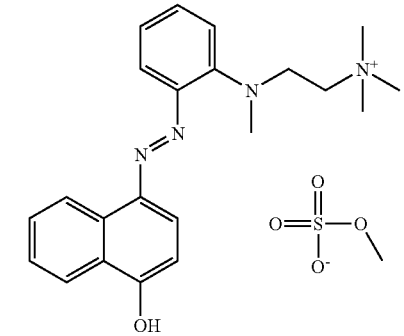

2-[{2-[(4-hydroxy-1-naphthalenyl)diazenyl]phenyl}(methyl)amino]-N,N,N-trimethylethanaminium methylsulfate (11)

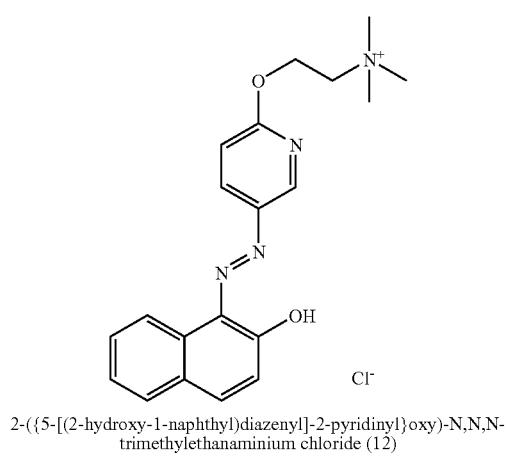

2-({5-[(2-hydroxy-1-naphthyl)diazenyl]-2-pyridinyl}oxy)-N,N,N-trimethylethanaminium chloride (12)

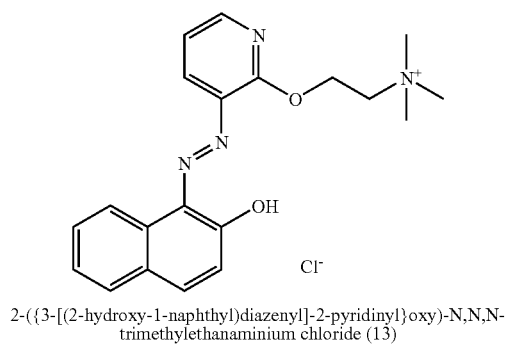

2-({3-[(2-hydroxy-1-naphthyl)diazenyl]-2-pyridinyl}oxy)-N,N,N-trimethylethanaminium chloride (13)

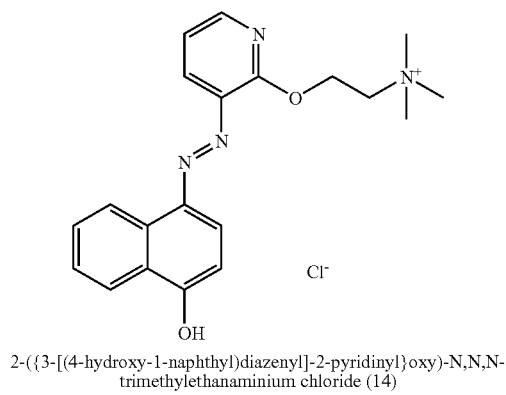

2-({3-[(4-hydroxy-1-naphthyl)diazenyl]-2-pyridinyl}oxy)-N,N,N-trimethylethanaminium chloride (14)

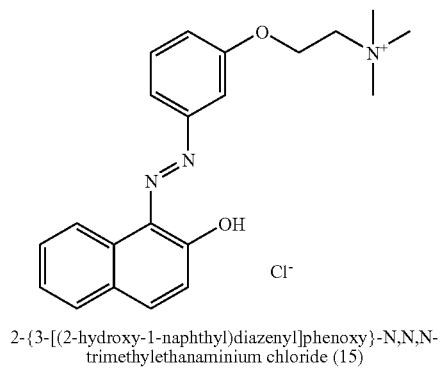

2-{3-[(2-hydroxy-1-naphthyl)diazenyl]phenoxy}-N,N,N-trimethylethanaminium chloride (15)

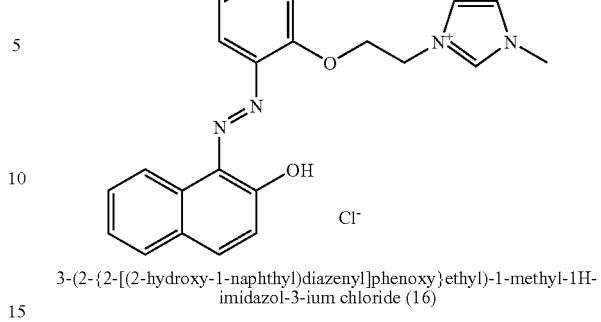

3-(2-{2-[(2-hydroxy-1-naphthyl)diazenyl]phenoxy}ethyl)-1-methyl-1H-imidazol-3-ium chloride (16)

The dyes of the invention of formula (I) are preferably prepared according to Scheme 1 the starting compounds used being, in particular, cationic nitroaromatic compounds of general formula (VI) described, for example, in German patent DE-A 2017497. Reduction of the nitro compounds, for example by catalytic hydrogenation, affords the amines of formula (VII) which are then diazotized by standard methods, preferably in water, and coupled with the desired 1- or 2-naphthol derivative.

Scheme 1

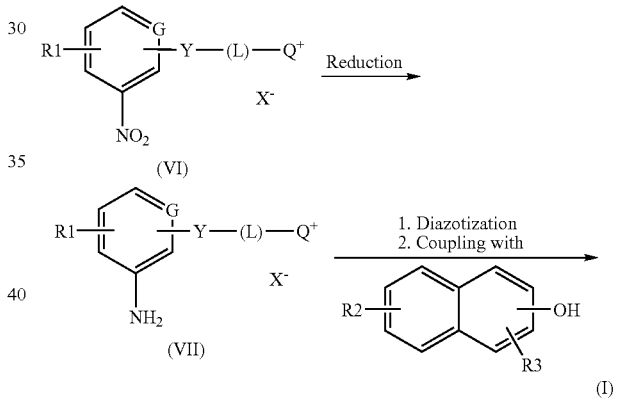

The dyes of formula (I) of the invention are eminently suited for use in colorants for keratin fibers, particularly hair.

Hence, the present patent application also has for an object colorants for keratin fibers containing at least one cationic naphthyldiazo dye of general formula (I).

The said colorants contain the cationic naphthyldiazo dyes of general formula (I) in a total amount from 0.01 to 10 weight percent and particularly from 0.1 to 6 weight percent.

Besides the dyes of formula (I), the colorant can contain other dyes and particularly 3-[(4,5-dihydro-3-methyl-5-keto-1-phenyl-1H-pyrazol-4-yl)azo]-N,N,N-trimethylbenzenaminium chloride, 3-[(3-methyl-5-hydroxy-1-phenyl-1H-pyrazol-4-yl)azo]trimethylammoniobenzene chloride (C.I. 12719; Basic Yellow 57), 8-[(4-aminophenyl)azo]-7-hydroxy-N,N,N-trimethyl-2-naphthalenaminium chloride (C.I. 12250; Basic Brown 16), 8-[(4-amino-3-nitrophenyl)azo]-7-hydroxy-N,N,N-trimethyl-2-naphthalenaminium chloride (C.I. 12251; Basic Brown 17), 8-[(4-amino-2-nitrophenyl)azo]-7-hydroxy-N,N,N-trimethyl-2-naphthalenaminium chloride (C.I. 12251:1; Basic Red 118), 7-hydroxy-N,N,N-trimethyl-8-{[2-(methyloxy)phenyl]-azo}-2-naphthalenaminium chloride (C.I. 12245; Basic Red 76), 3-[(4-amino-6-bromo-5,8-dihydro-1-hydroxy-8-imino-5-keto-2-naphthalenyl)amino]-N,N,N-trimethylbenzeneammonium chloride (C.I. 56059; Basic Blue 99) and N,N-dimethyl-3-{[4-(methylamino)-9,10-diketo-9,10-dihydro-1-anthracenyl]amino}-N-propyl-1-propanaminium bromide.

For the purpose of extending the range of colors, the colorant of the invention can additionally contain other natural or synthetic non-oxidative dyes. Suitable natural dyes are vegetable dyes, for example henna and indigo, whereas suitable synthetic non-oxidative dyes are, for example, other cationic dyes not represented by the afore-indicated formula (I), nitro dyes, azo dyes, triphenylmethane dyes and quinone dyes. Other suitable natural or synthetic non-oxidative dyes are, in particular, the following direct dyes: 9-(dimethylamino)benzo[a]phenoxazin-7-ium chloride (C.I.51175; Basic Blue 6), di[4-diethylamino)phenyl][4-ethylamino)-naphthyl]carbenium chloride (C.I. 42595; Basic Blue 7), 3,7-di(dimethylamino)-phenothiazin-5-ium chloride (C.I. 52015; Basic Blue 9), di[4(dimethylamino)-phenyl]-[4-(phenylamino)naphthyl]carbenium chloride (C.I. 44045; Basic Blue 26); 2-{[4-ethyl-(2-hydroxyethyl)aminophenyl]azo}-6-methoxy-3-methylbenzothiazolium methylsulfate (C.I. 11154; Basic Blue 41), 2,8-dimethyl-7-(dimethylamino)-3-imino-3H-phenoxazine monohydrochloride (Basic Blue 157), 7-(dimethylamino)-3-imino-2-methoxy-3H-phenoxazine monochloride (Basic Blue 124), bis[4-(dimethylamino)phenyl]-[4-(methylamino)phenyl]carbenium chloride (C.I. 42535; Basic Violet 1), 4-[(4-amino-3-methylphenyl)(4-imino-3-methyl-2,5-cyclohexadien-1-ylidene)-methyl]-2-methylbenzenamine hydrochloride (C.I. 42520; Basic Violet 2), tris[4-(dimethylamino)phenyl]carbenium chloride (C.I. 42555; Basic Violet 3), 2-[3,6-(diethylamino)dibenzopyranium-9-yl]benzoyl chloride (C.I. 45170; Basic Violet 10), di(4-aminophenyl)-(4-amino-3-methylphenyl)carbenium chloride (C.I. 42510; Basic Violet 14), 1,3-bis[(2,4-diamino-5-methylphenyl)azo]-3-methylbenzene (C.I. 21010; Basic Brown 4), 3,7-diamino-2,8-dimethyl-5-phenylphenazinium chloride (C.I. 50240; Basic Red 2), 1,4-dimethyl-5-{[4-(dimethylamino)phenyl]azo}-1,2,4-triazolium chloride (C.I. 11055; Basic Red 22), 3 (or 5)-{[4-(benzylmethylamino)phenyl]azo}-1,2-(or 1,4-) dimethyl-1,2,4-triazolium bromide (C.I. Basic Red 46 [sic]; 2-{[4-(dimethylamino)phenyl]azo}-1,3-dimethyl-1H-imidazol-3-ium chloride (Basic Red 51), 5-{[4-(dimethylamino)-phenyl]azo}-1,2-dimethyl-1H-pyrazol-2-ium chloride, 1,3-dimethyl-2-{[4-(methylamino)phenyl]azo}-1H-imidazol-3-ium chloride (Basic Red 109), 2-[(4-aminophenyl)azo]-1,3-dimethyl-1H-imidazol-3-ium chloride, 4-{[4-(dimethylamino)phenyl]azo}-1-methylpyridinium chloride, N,N-dimethyl-4-[(E)-(1-oxido-4-pyridinyl)diazenyl]aniline or 4-{[4-(dimethylamino)phenyl]azo}pyridine N-oxide, 2-{2-[(2,4-dimethoxyphenyl)amino]ethenyl}-1,3,3-trimethyl-3H-indol-1-ium chloride (C.I. 48055; Basic Yellow 11), 1-methyl-4-{[methyl(phenyl)-hydrazono]methyl}pyridinium chloride (Basic Yellow 87), 1-methyl-4-{(E)-[methyl-(4-methoxyphenyl)hydrazono]methyl}pyridinium chloride, 1-methyl-4-({methyl[4-methoxyphenyl]hydrazono}methyl)pyridinium methylsulfate (Basic Yellow 91) or bis[4-(diethylamino)phenyl]phenylcarbenium hydrogen sulfate (1:1) (C.I. 42040; Basic Green 1).

Although the dyes of formula (I) contained in the colorant of the invention have a cationic character, in special cases and depending on the dye carrier composition used they can also be employed in combination with anionic ("acid") dyes.

The total amount of other (particularly natural and/or synthetic non-oxidative) dyes in the colorant of the invention is from about 0.01 to 15 weight percent and particularly from about 0. to 12 weight percent.

The color intensity can be increased by addition of a carrier commonly used in cosmetic systems. Suitable compounds are described, for example, in DE-A 196 18 595 the disclosure of which is hereby included by reference. Particularly well suited carriers are, for example, benzyl alcohol, vanillin and isovanillin.

The colorant of the invention for dyeing keratin fibers can be, for example, in the form of a solution particularly an aqueous-alcoholic solution, or a cream, gel or emulsion. Suitable solvents besides water are, for example, the lower monohydric and polyhydric aliphatic alcohols, the esters and ethers thereof and mixtures of these solvents with one another or with water. The maximum boiling point of the afore-said suitable solvents is about 400° C., a boiling point of 20 to 250° C. being preferred.

It is also possible to dispense the colorant of the invention from a pressurized container as an aerosol spray or aerosol foam with the aid of an atomizer or some other suitable pumping or spraying device or in admixture with a conventional propellant liquefied under pressure.

The pH of the colorant of the invention is about 2 to 11, a pH of about 5 to 9 being particularly preferred. The pH is adjusted to an alkaline value preferably with ammonia, but an organic amine, for example monoethanolamine or triethanolamine, can also be used in place of ammonia. For adjustment to an acidic value, on the other hand, an organic or inorganic acid can be used, for example hydrochloric acid, sulfuric acid, phosphoric acid, ascorbic acid, glycolic acid or lactic acid.

Naturally, the afore-described colorants can optionally contain other additives commonly used for keratin fibers, for example hair-care agents, wetting agents, thickeners, softeners, preservatives and perfume oils as well as other additives indicated in the following.

Moreover, the colorant of the invention can contain wetting agents or emulsifiers from the classes of anionic, amphoteric, nonionic or zwitterionic surface-active substances, such as fatty alcohol sulfates, alkane sulfonates, alkylbenzene-sulfonates, alkylbetaines, α-olefin sulfonates, ethoxylated fatty alcohols, ethoxylated nonylphenols, fatty alkanolamines, ethoxylated fatty esters, fatty alcohol polyethylene glycol ether sulfates, alkylpolyglucosides, thickeners such as the higher fatty alcohols, starch, alginates, bentonites, cellulose derivatives, vaselines, paraffin oil, fatty acids, water-soluble polymeric thickeners such as the natural gum varieties guar gum and xanthan gum, furthermore carob bean flour, pectin, dextran, agar, amylose, amylopectin, dextrins, clays, or fully synthetic hydrocolloids, such as polyvinyl alcohol, furthermore hair-care agents such as lanolin derivatives, cholesterol, pantothenic acid, water-soluble polymers, protein derivatives, vitamins, plant extracts, sugar and betaine, auxiliary agents such as moisturizers, electrolytes, antioxidants, fatty amides, sequestering agents, film-forming agents and preservatives.

The afore-described colorant can also contain natural or synthetic polymers or modified polymers of natural origin whereby the keratin fibers are dyed and fixed at the same time. Such agents are generally referred to as tinting fixatives or dye fixatives. Synthetic polymers known to be used for this purpose in the cosmetic field are, for example, polyvinylpyrolidone, polyvinyl acetate, polyvinyl alcohol and polyacrylic compounds, such as polyacrylic acid, polymethacrylic acid, polyacrylonitrile, polyvinyl acetates and the copolymers of such compounds, for example polyvinylpyrrolidone-vinyl acetate. Suitable natural polymers of modified natural polymers are, for example, chitosan (deacetylated chitin) or chitosan derivatives.

The indicated constituents are used in amounts commonly employed for such purposes, for example the wetting agents and emulsifiers at a concentration of about 0.5 to 30 weight percent, the thickeners in an amount from about 0.1 to 25 weight percent and the hair-care agents in an amount from about 0.1 to 5 weight percent. The afore-said polymers can be used in the colorant of the invention in amounts commonly added to such colorants, particularly in an amount from about 1 to 5 weight percent.

The agents of the invention for dyeing keratin fibers are particularly well suited for dyeing hair. To this end, the colorant of the invention is applied to the hair in the usual manner in an amount sufficient for hair dyeing, in general in an amount from about 50 to 150 grams. After an exposure time sufficient for hair dyeing, usually about 10 to 45 minutes at 20 to 50° C. and preferably about 15 to 30 minutes at about 40° C., the hair is rinsed with water, optionally washed with a shampoo and/or with an aqueous solution of a weak organic acid, for example citric acid or tartaric acid, post-rinsed and dried.

The colorant which also exerts a fixing action is used in the known and usual manner by moistening the hair with a fixative, styling the hair into a hairdo and then drying.

With the colorant of the invention, it is possible to achieve color shades in both the natural and the trendy range (for example highly fashionable, bright shades). Moreover, besides the said color shades it is also possible to achieve a number of brilliant color reflections over the entire visible range. As a result of the very high tinting power of these dyes and their high substantivity, the original color of the fiber can be covered in outstanding fashion. In this manner, the initially mentioned desire to integrate the color into the fashion and to express a personality can be fully satisfied. The outstanding properties of the novel colorant manifest themselves particularly on light-damaged and weathering-damaged or permanently waved hair. In particular, the colorations obtained show very good permanence and resistance to washing.

The following examples will explain the subject matter of the invention in greater detail without limiting it to the examples given.

EXAMPLES

Example 1

Preparation of 2-{2-[(2-hydroxy-1-naphthyl)diazenyl]phenoxy}-N,N,N-trimethylethanaminium methylsulfate Step 1.1 Preparation of 2-(2-aminophenoxy)-N,N,N-trimethylethanaminium methylsulfate 34 g (100 mmol) of N,N,N-trimethyl-2-(2-nitrophenoxy) ethanaminium methylsulfate obtained as described in DE-A 20 17 497 in 300 mL of ethanol was hydrogenated in the presence of 3.4 g of Pd/C (10%) under 9 bar of hydrogen pressure. After 2 hours, the catalyst was filtered off and the filtrate was evaporated to dryness. This gave a colorless oil that gradually solidified.

Yield: 31 g (100% of the theoretical)

$^1$H-NMR (DMSO-$d_6$): δ=6.85 ppm (d, 1H); 6.70 ppm (m, 2H); 6.52 ppm (m, 1H); 4.82 ppm (broad s, 2H); 4.39 ppm (broad s, 2H); 3.79 ppm (broad s, 2H); 3.38 ppm (s, 3H); 3.19 ppm (s, 9H).

Step 1.2 Preparation of 2-{2-[(2-hydroxy-1-naphthyl)diazenyl]phenoxy}-N,N,N-trimethylethanaminium methylsulfate 15.6 g (50 mmol) of the compound obtained in Step 1.1 was dissolved in 160 mL of water and 18.3 g of a 32% hydrochloric acid solution, and the resulting mixture was diazotized with 4.2 g (60 mmol) of sodium nitrite in 25 mL of water with cooling in an ice bath while keeping the temperature from exceeding 5° C. The mixture was allowed to agitate for an additional hour after which excess nitrite was decomposed by addition of sulfaminic acid. The diazonium salt solution was then poured into a solution of 7.4 g (51 mmol) of 2-naphthol in 50 mL of isopropanol with agitation. The pH was adjusted to 9 to 10 by addition of saturated sodium carbonate solution which brought about coupling with formation of a thick dye slurry. Agitation was continued for an additional 30 minutes after which the mixture was suction-filtered. The crude product was then taken up in 300 mL of 60° C. water, neutralized with 2-normal hydrochloric acid, cooled and again suction-filtered. Drying gave 13 g (55% of the theoretical) of a red product.

$^1$H-NMR (DMSO-$d_6$): δ=8.51 (d, 1H); 8.08 (d, 1H); 7.91 (d, 1H); 7.73 (d, 1H); 7.58 (t, 1H); 7.43 (t, 1H); 7.37 (m, 2H); 7.22 (m, 1H); 6.80 (d, 1H); 4.72 (t, 2H); 3.96 (t, 2H); 3.32 ppm (s, 12H).

Example 2

Preparation of 2-{2-[(4-hydroxy-1-naphthyl)diazenyl]-phenoxy}-N,N,N-trimethylethanaminium chloride The method was the same as in Example 1, but instead of 2-naphthol the same amount of 1-naphthol was used.

Yield: 11.8 g (50% of the theoretical)

$^1$H-NMR (DMSO-$d_6$): δ=8.77 ppm (d, 1H); 8.22 ppm (dd, 1H); 7.86 ppm (d, 1H); 7.72 ppm (dd, 1H); 7.45 ppm (m, 1H); 7.26 ppm (m, 2H); 7.20 ppm (d, 1H); 7.08 ppm (m, 1H); 6.41 ppm (d, 1H); 4.60 ppm (t, 2H); 3.88 ppm (t, 2H); 3.28 ppm (s, 9H).

Example 3

Preparation of 2-(2-{2-[(2-hydroxy-1-naphthyl)diazenyl]-phenoxy}ethyl)-1-methylpyridinium methylsulfate Step 3.1 Preparation of 2-[2-(2-nitrophenoxy)ethyl]pyridine 7.05 g (50 mmol) of 2-fluoronitrobenzene, 6.77 g (50 mmol) of 2-(2-hydroxyethyl)pyridine and 16.62 g (50 mmol) of cesium carbonate in 30 mL of dimethyformamide were stirred at room temperature for 7 days. The mixture was then filtered, and the filtrate was subjected to fractional distillation. The solvent and unreacted 2-fluoronitrobenzene distilled below 100° C. at 8 to 4 mbar. The product distilled in a bulb tube still at 170 to 180° C. of furnace temperature under a vacuum of 3 mbar.

Yield: 8.7 g (71% of the theoretical)

¹H-NMR (DMSO-d₆): δ=8.50 ppm (d, 1H); 7.82 ppm (dd, 1H); 7.69 ppm (dt, 1H); 7.61 ppm (dt, 1H); 7.36 ppm (m, 2H); 7.22 ppm (t, 1H); 7.07 ppm (t, 1H); 4.53 ppm (t, 2H); 3.20 ppm (t, 2H).

Step 3.2 Preparation of 1-methyl-2-[2-(2-nitrophenoxy)ethyl]pyridinium methylsulfate 4.88 g (20 mmol) of the compound from Step 3.1 was dissolved with agitation in 60 mL of ethyl acetate and to the solution was added 2.78 g (20 mmol) of dimethyl sulfate. A colorless precipitate formed gradually. The mixture was allowed to agitate for an additional 4 hours at room temperature after which it was filtered, and the filter cake was washed with a small amount of ethyl acetate and then dried at 40° C. under vacuum.

Yield: 6 g (81% of the theoretical), colorless product

¹H-NMR (DMSO-d₆): δ=9.06 ppm (d, 1H); 8.55 ppm (dt, 1H); 8.12 ppm (d, 1H); 8.02 ppm (dt, 1H); 7.71 ppm (dd, 1H); 7.69 ppm (dt, 1H); 7.42 ppm (d, 1H); 7.15 ppm (dt, 1H); 4.65 ppm (t, 2H); 4.37 ppm (s, 3H); 3.65 ppm (t, 2H); 3.37 ppm (s, 3H).

Step 3.3 Preparation of 2-[2-(2-aminophenoxy)ethyl]-1-methylpyridinium methylsulfate 3.7 g (10 mmol) of the compound from Step 3.2 was hydrogenated in 25 mL of water in the presence of 0.3 g of Pd/C (10%) under 9 bar of hydrogen pressure. After 2 hours, the catalyst was filtered off, and the solution obtained was directly subjected to further reaction.

Step 3.4 Preparation of 2-(2-{2-[(2-hydroxy-1-naphthyl)diazenyl]phenoxy}ethyl-1-methylpyridinium methylsulfate To the solution from Step 3.3 (10 mmol) was added 2.9 g of 32% hydrochloric acid solution. Then, in an ice bath, 0.7 g (10 mmol) of sodium nitrite dissolved in 5 mL of water was added dropwise over a period of 10 minutes without allowing the temperature to exceed 5° C. The mixture was allowed to agitate in the ice bath for an additional hour after which unreacted nitrite was decomposed by addition of sulfaminic acid. The resulting solution was then added to a solution of 1.45 g (10 mmol) of 2-naphthol in 15 mL of water, 15 mL of isopropanol and 3.4 g of 30% sodium hydroxide solution. The azo coupling took place spontaneously with formation of a thick, red slurry. The mixture was allowed to agitate for an additional hour after which it was suction-filtered. The resulting dye was dried at 40° C. under vacuum.

Yield: 3.65 g (95% of the theoretical), dark-red product

¹H-NMR (DMSO-d₆): δ=8.51 ppm (m, 1H); 8.49 ppm (d, 1H); 8.04 ppm (d, 1H); 7.92 ppm (d, 1H); 7.70 ppm (m, 2H); 7.56 ppm (m, 2H); 7.47 ppm (t, 1H); 7.29 ppm (m, 2H); 7.23 ppm (m, 1H); 7.12 ppm (m, 1H); 6.84 ppm (d, 1H); 4.56 ppm (t, 2H); 3.33 ppm (t, overlap with water signal, 2H).

Example 4

Preparation of 2-{2-[(2,7-dihydroxy-1-naphthyl)diazenyl]-phenoxy}-N,N,N-trimethylethanaminium chloride The method was the same as in Example 1, but with 8.0 g (50 mmol) of 2,7-dihydroxynaphthalene used in place of 2-naphthol.

Yield: 16.10 g (80% of the theoretical), dark-red product

¹H-NMR (DMSO-d₆): δ=10.12 ppm (s, 1H); 8.00 ppm (d, 1H); 7.81 ppm (d, 1H); 7.80 ppm (d, 1H); 7.56 ppm (d, 1H); 7.32 ppm (m, 2H); 7.22 ppm (t, 1H); 6.91 ppm (dd, 1H); 6.53 ppm (d, 1H); 4.70 ppm (t, 2H); 3.95 ppm (t, 2H); 3.37 ppm (s, 9H).

Example 5

Preparation of 4-(2-{2-[(2-hydroxy-1-naphthyl)diazenyl]phenoxy}ethyl)-4-methylmorpholin-4-ium chloride Step 5.1: Preparation of 4-[2-(2-nitrophenoxy)ethyl]morpholine As in Example 1 of WO 00/59883, 14.11 g (100 mmol) of 2-fluoronitrobenzene, 14.45 g (100 mmol) of morpholinoethanol, 35.8 g (100 mmol) of cesium carbonate and 100 mL of dimethylformamide were allowed to agitate at room temperature for 7 days. The mixture was then filtered, the dimethylformamide was removed in a rotary evaporator, and the residue was distilled in a bulb tube still at 4 mbar and a furnace temperature of 160 to 170° C.

Yield: 17.8 g (70.6% of the theoretical), yellowish oil

¹H-NMR (DMSO-d₆): δ=7.85 ppm (d, 1H); 7.64 ppm (t, 1H); 7.38 ppm (d, 1H); 7.11 ppm (t, 1H); 4.27 ppm (t, 2H); 3.55 ppm (m, 4H); 2.70 ppm (t, 2H).

Step 5.2: Preparation of 4-methyl-4-[2-(2-nitrophenoxy)ethyl]morpholin-4-ium methylsulfate 2.52 g (10 mmol) of the product from Step 5.1 was dissolved in 30 mL of ethyl acetate, 1.4 g (11 mmol) of dimethyl sulfate was added and the mixture was allowed to agitate at room temperature which caused the formation of a precipitate. After 4 hours, the mixture was filtered, and the filter cake was washed with a small amount of ethyl acetate. Drying at 40° C. under vacuum gave 2.3 g (61% of the theoretical) of a beige-colored, slightly sticky product.

¹H-NMR (DMSO-d₆): δ=7.94 ppm (dd, 1H); 7.73 ppm (dt, 1H); 7.42 ppm (d, 1H); 7.20 ppm (dt, 1H); 4.69 ppm (t, 2H); 4.02 ppm (t, 2H); 3.96 ppm (m, 4H); 3.55 ppm (m, 4H); 3.38 ppm (s, 3H); 3.30 ppm (s, 3H).

Step 5.3: Preparation of 4-[2-(2-aminophenoxy)ethyl]-4-methylmorpholin-4-ium methylsulfate 2.08 g (5.5 mmol) of the compound from Step 5.2 was dissolved in 80 mL of ethanol and hydrogenated in the presence of 0.25 g of Pd/C (10%) under 9 bar of hydrogen pressure. After 2 hours, the catalyst was filtered off and the filtrate was evaporated to dryness. This gave 1.9 g (99% of the theoretical) of a colorless oil which was subjected to further reaction without additional purification.

Step 5.4: Preparation of 4-(2-{2-[(2-hydroxy-1-naphthyl)diazenyl]phenoxy}ethyl)-4-methylmorpholin-4-ium chloride 1.5 g (4.3 mmol) of the compound from Step 5.3 was dissolved in 30 mL of water and 1.3 g of 32% hydrochloric acid solution. At 0 to 5° C., 0.31 g (4.5 mmol) of sodium nitrite in 3 mL of water was added dropwise without allowing the temperature to exceed 5° C. After one hour of additional agitation in the ice bath, excess sodium nitrite was decomposed with sulfaminic acid, and the mixture was poured with agitation into a solution of 0.65 g (4.3 mmol) of 2-naphthol in 8 mL of isopropanol. To this mixture was added a saturated solution of sodium carbonate until the pH reached a value of 9. The mixture was then allowed to agitate for an additional 30 min after which it was neutralized with dilute hydrochloric acid and suction-filtered. The resulting crude product was suspended in 20 mL of 2-normal hydrochloric acid at room temperature for 15 minutes after which the mixture was suction-filtered and dried.

Yield: 1.75 g (95% of the theoretical), red dye
$^1$H-NMR (DMSO-$d_6$): δ=8.50 ppm (d, 1H); 8.11 ppm (d, 1H); 7.96 ppm (d, 1H); 7.76 ppm (d, 1H); 7.61 ppm (t, 1H); 7.49 ppm (t, 1H); 7.34 ppm (m, 1H); 7.22 ppm (t, 2H); 6.82 ppm (d, 1H); 4.75 ppm (t, 2H); 4.11 ppm (t, 2H); 4.01 ppm (m, 4H); 3.69 ppm (m, 4H); 3.43 ppm (s, 3H).

Example 6

Preparation of 2-({2-[(2,4-dihydroxy-1-naphthalenyl)diazenyl]phenyl}oxy)-N,N,N-trimethylethanaminium chloride 1.56 g (5 mmol) of the compound from Step 1.1 was dissolved in 20 mL of water and 1.85 g of hydrochloric acid (32%) and diazotized with 0.42 g (6 mmol) of sodium nitrite in 3 mL of water with cooling in an ice bath while not allowing the temperature to exceed 5° C. The mixture was allowed to agitate for an additional hour after which excess nitrite was decomposed by addition of sulfaminic acid. The diazonium salt solution was poured with agitation into a solution of 0.8 g (5 mmol) of 1,3-dihydroxynaphthalene in 30 mL of isopropanol. The pH was adjusted to 9 to 10 by addition of saturated sodium carbonate solution which caused coupling to take place with formation of a thick dye slurry. The slurry was allowed to agitate for an additional 30 min and was then suction-filtered. The crude product was dissolved in 30 mL of 60° C. water and the pH was adjusted to 1 with hydrochloric acid (32%). This caused the dye to precipitate as the chloride. The mixture was allowed to cool and was then again suction-filtered. Drying gave 18 g (89% of the theoretical) of an orange-colored product.

$^1$H-NMR (DMSO-$d_6$): δ=10.09 (s, 1H); 9.48 (s, 1H); 8.40 (d, 1H); 8.00 (d, 1H); 7.93 (d, 1H); 7.62 (t, 1H); 7.49 (t, 1H); 7.20 (m, 3H); 6.20 (s, 1H); 4.66 (t, 2H); 3.93 (t, 2H); 3.32 ppm (s, 9H).

Example 7

Preparation of 2-[(2-{[2-hydroxy-7-(methyloxy)-1-naphthalenyl]diazenyl}phenyl)oxy]-N,N,N-trimethylethanaminium chloride The diazonium salt was prepared as in Example 6 and then coupled with 0.87 g (5 mmol) of 7-methoxy-2-naphthol.

Yield: 1.1 g (77% of the theoretical), red dye
$^1$H-NMR (DMSO-$d_6$): δ=8.11 (d, 1H); 7.90 (d, 1H); 7.86 (d, 1H); 7.70 (d, 1H); 7.32 (m, 2H); 7.21 (t, 1H); 7.08 (dd, 1H); 6.65 (d, 1H); 4.71 (m unstructured, 2H), 3.95 (m unstructured, 2H); 3.33 (s, 9H); 3.31 ppm (s, 3H).

Example 8

Preparation of 2-{[2-({2-hydroxy-3-[(phenylamino)carbonyl]-1-naphthalenyl}diazenyl)phenyl]oxy}-N,N,N-trimethylethanaminium chloride The diazonium salt was prepared as in Example 6 and then coupled with 1.32 g (5 mmol) of 3-hydroxy-2-naphthanilide.

Yield: 1.3 g (51% of the theoretical), red-violet dye $^1$H-NMR (DMSO-$d_6$): δ=8.89 (s, 1H); 8.53 (s, 1H), 8.19 (d, 1H); 8.01 (d, 1H); 7.92 (d, 1H); 7.86 (d, 1H); 7.74 (m, 3H); 7.52 (m, 1H); 7.38 (m, 4H); 7.15 (m, 2H); 4.77 (m unstructured, 2H); 4.07 (m unstructured, 2H).

Example 9

Preparation of 2-[{4-[(2-hydroxy-1-naphthalenyl)diazenyl]phenyl}(methyl)amino]-N,N,N-trimethylethanaminium methylsulfate Step 9.1: Preparation of N,N,N'-trimethyl-N'-(4-nitrophenyl)-1,2-ethanediamine 7.05 g (50 mmol) of 4-fluoronitrobenzene and 8.17 g (80 mmol) of N,N,N'-trimethylethylenediamine were dissolved in 50 mL of toluene which caused a slight increase in temperature. At the end of the exotherm, the mixture was heated at 80° C. for 10 hours. The solvent was then removed in a rotary evaporator, and the oily residue was dissolved in 80 mL of 3-molar ethanolic hydrochloric acid. Stirring in an ice bath gradually resulted in crystallization. After 1 hour, the resulting crystalline slurry was suction-filtered and the filter cake was washed with a small amount of ice-cold ethanol and then dried at 40° C. under vacuum.

Yield: 11.0 g (85% of the theoretical), bright-yellow crystals.

$^1$H-NMR (DMSO-$d_6$): δ=8.06 (d, 2H); 6.94 (d, 2H); 3.93 (t, 2H); 3.24 (t, 2H); 3.10 (s, 3H); 2.78 ppm (s, 6H).

To prepare the free base, 10 g of the afore-described product was dissolved in 50 mL of water, the pH was adjusted to 10 by addition of saturated sodium carbonate solution, and the resulting solution was extracted three times with 25-mL portions of ethyl acetate. The combined organic phases were dried over magnesium sulfate and then evaporated to dryness. This gave 8.0 g (93% of the theoretical) of a yellow oil.

$^1$H-NMR (DMSO-$d_6$): δ=8.02 (d, 2H); 6.74 (d, 2H); 3.55 (t, 2H); 3.06 (s, 3H); 2.40 (t, 2H); 2.18 ppm (s, 6H).

Step 9.2: Preparation of N,N,N-trimethyl-2-[methyl (4-nitrophenyl)-amino]ethanaminium methylsulfate 8.0 g (36 mmol) of the compound from Step 9.1 was dissolved in 50 mL of acetonitrile and to the solution was added dropwise 4.55 g (36 mmol) of dimethyl sulfate over a period of 5 minutes with agitation which caused the reaction mixture to warm up slightly while the product gradually separated in crystalline form. The mixture was allowed to agitate for an additional 3 hours at room temperature after which it was suction-filtered. The filter cake was washed with a small amount of acetonitrile and then dried at 40° C. under vacuum. This gave 11.0 g (88% of the theoretical) of yellow crystals.

$^1$H-NMR (DMSO-$d_6$): δ=8.10 (d, 2H); 6.90 (d, 2H); 3.97 (t, 2H); 3.52 (t, 2H); 3.39 (s, 3H); 3.17 (s, 9H); 3.14 ppm (s, 3H).

Step 9.3: Preparation of 2-[(4-aminophenyl)(methyl)amino]-N,N,N-trimethylethanaminium methylsulfate 10 g (28.6 mmol) of the compound from Step 9.2 was dissolved in 80 mL of water and hydrogenated in the presence of 1 g of Pd/C (10%) under 9 bar of hydrogen pressure. After 2 hours, the catalyst was filtered off and the filtrate was evaporated to dryness. This gave 9.3 g (99.6% of the theoretical) of a brown oil.

$^1$H-NMR (DMSO-d$_6$): δ=6.65 (d, 2H); 6.53 (d, 2H); 4.56 (s broad, 2H); 3.51 (m unstructured, 2H); 3.39 (s, 3H); 3.37 (m unstructured, 2H); 3.11 ppm (s, 9H).

Step 9.4: Preparation of 2-[{4-[(2-hydroxy-1-naphthalenyl)diazenyl]phenyl}(methyl)amino]-N,N,N-trimethylethanaminium methylsulfate 1.6 g (5 mmol) of the compound from Step 9.3 was dissolved in 20 mL of water and 1.7 g of hydrochloric acid (32%) and to the solution was added dropwise with agitation, in an ice bath, 0.35 g (5 mmol) of sodium nitrite in 2 mL of water. The mixture was allowed to agitate in the ice bath for an additional 30 minutes after which a few drops of 10% sulfaminic acid solution was added and the mixture was poured into a solution of 0.72 g (5 mmol) of 2-naphthol in 8 mL of isopropanol. The pH was then increased to 9 by addition of saturated sodium carbonate solution which resulted in the formation of a brown solution. After 30 min, the mixture was neutralized by addition of 2-normal hydrochloric acid and, to isolate the dye, evaporated to dryness in a rotary evaporator. The residue was then taken up in 80 mL of methanol, the inorganic salts were filtered off and the solution was concentrated to a total volume of about 10 ml. The addition of about 30 mL of isopropanol caused the dye to precipitate.

Yield: 1.5 g (63% of the theoretical), red-brown product.

$^1$H-NMR (DMSO-d$_6$): δ=8.75 (d, 2H); 7.90 (m, 4H); 7.63 (t, 1H); 7.46 (t, 1H); 7.17 (d, 1H); 6.98 (d, 2H); 3.97 (t, 2H); 3.57 (t, 2H); 3.38 (s, 3H); 3.21 (s, 9H); 3.14 ppm (s, 3H).

Example 10

Preparation of 2-[{2-[(2-hydroxy-1-naphthalenyl)diazenyl]phenyl}(methyl)amino]-N,N,N-trimethyl-ethanaminium methylsulfate Step 10.1: Preparation of N,N,N'-trimethyl-N'-(2-nitrophenyl)-1,2-ethanediamine hydrochloride 7.05 g (50 mmol) of 2-fluoronitrobenzene was dissolved in 50 mL of toluene. To this solution was added dropwise over a period of 5 minutes and with agitation 8.20 g (80 mmol) of N,N,N'-trimethylethylenediamine which caused the reaction mixture to warm up to about 40° C. Following the exotherm, the mixture was heated at 80° C. for 10 hours after which it was cooled, and the solvent was removed in a rotary evaporator. This gave an oily residue to which 80 mL of 3-molar ethanolic hydrochloric acid was added, and the resulting mixture was allowed to agitate in an ice bath for one hour. This gradually produced an orange-colored precipitate which was suction-filtered off and washed with a small amount of cold ethanol. Drying at 40° C. under vacuum gave 7 g (69% of the theoretical) of an orange-colored powder.

$^1$H-NMR (DMSO-d$_6$): δ=10.90 (s broad, 1H); 7.81 (dd, 1H); 7.57 (m, 1H); 7.42 (dd, 1H); 7.08 (dt, 1H); 3.57 (t, 2H); 3.24 (t, 2H); 2.75 (s, 6H); 2.72 PPM (s, 3H).

Step 10.2: Preparation of N,N,N'-trimethyl-N'-(2-nitrophenyl)-1,2-ethanediamine 6.50 g (25 mmol) of the compound from Step 10.1 was dissolved in 50 mL of water and rendered alkaline with saturated sodium carbonate solution. The solution was then extracted three times with 20-mL portions of ethyl acetate, and the combined organic phases were dried over magnesium sulfate. The solution was evaporated which gave 5.3 g (95% of the theoretical) of a yellow oil.

$^1$H-NMR (DMSO-d$_6$): δ=7.71 (dd, 1H); 7.49 (t with fine line splitting, 1H); 7.24 (dd, 1H); 6.91 (t with fine line splitting, 1H); 3.19 (t, 2H); 2.78 (s, 3H); 2.40 (t, 2H); 2.11 ppm (s, 6H).

Step 10.3: Preparation of N,N,N-trimethyl-2-[methyl(2-nitrophenyl)amino]-ethanaminium methylsulfate 5.0 g (22.4 mmol) of the free amine from Step 10.2 was dissolved in 50 ml of acetonitrile and to this solution was added dropwise with agitation over a period of 10 min 2.83 g (22.4 mmol) of dimethyl sulfate. The reaction temperature gradually rose to 45° C. and a precipitate formed. After an agitation period of 3 hours, the mixture was filtered and the filter cake was washed with a small amount of acetonitrile and then dried at 40° C. under vacuum.

Yield: 4.8 g (61% of the theoretical), yellowish powder.

$^1$H-NMR (DMSO-d$_6$): δ=7.82 (dd, 1H); 7.61 (t with fine line splitting, 1H); 7.44 (dd, 1H); 7.14 (t with fine line splitting, 1H); 3.58 (m, 4H); 3.38 (s, 3H); 3.12 (s, 9H); 2.76 ppm (s, 3H).

Step 10.4: Preparation of 2-[(2-aminophenyl)(methyl)amino]-N,N,N-trimethylethanaminium methylsulfate 4.5 g (12.9 mmol) of the compound from Step 10.3 was dissolved in 80 mL of water and hydrogenated for 2 hours in the presence of 0.3 g of Pd/C (10%) under a hydrogen pressure of 9 bar. The catalyst was then filtered off, and the filtrate was evaporated to dryness. This gave 4.1 g (99% of the theoretical) of a violetish oil.

$^1$H-NMR (DMSO-d$_6$): δ=7.00 (dd, 1H); 6.82 (t with fine line splitting, 1H); 6.70 (dd, 1H); 6.56 (t with fine line splitting, 1H); 4.83 (s, 2H); 3.44 (t, 2H); 3.39 (s, 3H); 3.26 (t, 2H); 3.09 (s, 9H); 2.57 ppm (s, 3H).

Step 10.5: Preparation of 2-[{2-hydroxy-1-naphthalenyl)diazenyl]phenyl}-(methyl)amino]-N,N,N-trimethylethanaminium methylsulfate 1.4 g (4.4 mmol) of the compound from Step 10.4 was dissolved in 20 mL of water and 1.5 g of hydrochloric acid (32%), the solution was cooled in an ice bath and to it was added over a period of 10 min 0.3 g (4.4 mmol) of sodium nitrite in 2 mL of water. The mixture was allowed to agitate for an additional 30 min after which a solution of 0.63 g (4.4 mmol) of 2-naphthol in 10 mL of isopropanol was added. The pH was adjusted to 8 to 9 by addition of saturated sodium carbonate solution which resulted in coupling with formation of a brown solution. After 1 hour, the solution was evaporated to dryness and, to isolate the pure dye, 80 mL of methanol was added to the residue. After an agitation period of 1 hour at room temperature, the inorganic salts were filtered off. The filtrate was concentrated to about 20% of its original volume and then 30 mL of isopropanol was added to induce crystallization. Cooling in an ice bath, filtration and drying at 40° C. under vacuum gave 1.6 g (67% of the original) of a red-brown product.

$^1$H-NMR (DMSO-d$_6$): δ=8.48 (d, 1H); 8.10 (d with fine line splitting), 1H); 7.93 (d, 1H); 7.74 (d, 1H); 7.60 (t with fine line splitting, 1H); 7.46 (m, 2H); 7.35 (m, 2H); 6.78 (d, 1H); 3.55 (m, 4H); 3.38 (s, 3H); 3.14 (s, 9H); 2.78 ppm (s, 3H).

Example 11

Preparation of 2[{2-[(4-hydroxy)-1-naphthalenyl)diazenyl]-phenyl}(methyl)amino]-N,N,N-trimethylethanaminium methylsulfate The method was the same as in Example 9, Step 9.4, but 0.63 g (4.4 mmol) of 1-naphthol was used instead of 2-naphthol.

Yield: 1.2 g (57% of the theoretical)

$^1$H-NMR (DMSO-$d_6$): δ=8.71 (d, 1H); 8.13 (d, 1H); 7.89 (d, 1H); 7.58 (dd, 1H); 7.43 (t with fine line splitting, 1H); 7.22 (t, 1H); 7.12 (m, 2H); (t with fine line splitting, 1H); 6.30 (d, 1H); 3.64 (m, 4H); 3.35 (s, 3H); 3.03 (s, 9H); 2.97 ppm (s, 3H).

Example 12

Preparation of 2-({5-[(2-hydroxy-1-naphthyl)diazenyl]-2-pyridinyl}oxy)-N,N,N-trimethylethanaminium chloride

Step 12.1 Preparation of N,N-dimethyl-2-[(5-nitro-2-pyridinyl)oxy]-ethanamine A mixture of 7.93 g (50 mmol) of 2-chloro-5-nitropyridine, 4.9 g (55 mmol) of 2,2-dimethylaminoethanol and 4 g (29 mmol) of potassium carbonate in 50 mL of dimethylformamide was allowed to stand at room temperature with occasional shaking. The mixture was then poured into 200 mL of water and the resulting mixture was extracted three times with 30-mL portions of ethyl acetate. Drying over magnesium sulfate and evaporation of the solvent gave a yellowish oil.

Yield: 4.9 g (46% of the theoretical)

$^1$H-NMR (DMSO-$d_6$): δ=9.07 (d, 1H); 8.46 (dd, 1H); 7.04 (d, 1H); 4.48 (t, 2H); 2.64 (t, 2H); 2.20 ppm (s, 6H).

Step 12.2 Preparation of N,N,N-trimethyl-2-[(5-nitro-2-pyridinyl)oxy]-ethanaminium methylsulfate 4.4 g (21 mol) of the compound from Step 12.1 was dissolved in 50 mL of ethyl acetate and to the resulting mixture was added 2.65 g (21 mmol) of dimethyl sulfate over a period of 5 min with agitation. A precipitate was formed as a result of a slightly exothermic reaction. The mixture was allowed to agitate for an additional hour after which it was suction-filtered. The filter cake was then washed with ethyl acetate and dried at 40° C. under vacuum which gave 6.5 g (92% of the theoretical) of colorless crystals.

$^1$H-NMR (DMSO-$d_6$): δ=9.13 (d, 1H); 8.56 (dd, 1H); 7.12 (d, 1H); 4.86 (m, 2H); 3.84 (m, 2H); 3.37 (s, 3H); 3.18 ppm (s, 9H).

Step 12.3 Preparation of 2-[(5-amino-2-pyridinyl)oxy]-N,N,N-trimethylethanaminium methylsulfate 4.0 g (12 mmol) of the compound from Step 12.2 in 80 mL of water was hydrogenated in the presence of 0.4 g of Pd/C (10%) under 9 bar of hydrogen pressure. After 3 hours the catalyst was filtered off and the water was removed in a rotary evaporator.

Yield: 3.6 g (98.5% of the theoretical), violetish oil $^1$H-NMR (DMSO-$d_6$): δ=7.52 (d, 1H); 7.05 (dd, 1H); 6.61 (d, 1H); 4.87 (s, 2H); 4.56 (m, 2H); 3.71 (m, 2H); 3.38 (s, 3H); 3.15 ppm (s, 9H).

Step 12.4 Preparation of 2-({5-[(2-hydroxy-1-naphthyl)diazenyl]-2-pyridinyloxy}-N,N,N-trimethylethanaminium chloride 1.81 g (5.9 mmol) of the compound from Step 12.3 was dissolved in 30 mL of water and 2.4 g of hydrochloric acid (32%) and to this solution was added dropwise in an ice bath, at 0 to 5° C., a solution of 0.41 g (6 mmol) of sodium nitrite. The mixture was allowed to agitate in the ice bath for an additional 30 min after which excess nitrite was decomposed by addition of sulfaminic acid. The resulting diazonium salt solution was added to a solution of 0.87 g (6 mmol) of 2-naphthol in 10 mL of isopropanol, and for coupling the pH was adjusted to 8 to 9 by addition of saturated sodium carbonate solution. The coupling was allowed to proceed for an additional hour after which the mixture was neutralized with 2-normal hydrochloric acid and the precipitate was suction-filtered off. Compressing the filter cake and drying it at 40° C. under vacuum gave 1.7 g (74% of the theoretical) of a bright-orange product.

$^1$H-NMR (DMSO-$d_6$): δ=14.55 (s broad, 1H); 8.91 (d, 1H); 8.75 (d, 1H); 8.47 (dd, 1H); 8.03 (d, 1H); 7.90 (d, 1H); 7.65 (t, 1H); 7.50 (t, 1H); 7.16 (d, 1H): 7.11 (d, 1H); 4.85 (m unstructured, 2H); 3.86 (m, 2H); 3.22 ppm (s, 9H).

Example 13

Hair Colorant

A colorant having the following composition was prepared:

| | |
|---|---|
| 4.0 g | of decylglucoside |
| 5.0 g | of ethanol |
| 0.0025 mol | of dye as per Table 1 |
| to 100.0 g | water, demineralized |

The pH of the colorant was adjusted to 7 with phosphoric acid or sodium hydroxide. The colorant was then applied to bleached hair and after an exposure time of 20 min at 40° C. it was rinsed out with water. After drying, the colorants indicated in Table 1 were obtained.

TABLE 1

| Dye as per | L* | a* | b* | Color |
|---|---|---|---|---|
| Example 1 | 44.35 | 54.77 | 45.12 | bright orange red |
| Example 2 | 35.43 | 33.64 | 29.64 | red-brown |
| Example 3 | 46.65 | 48.57 | 39.20 | bright orange red |
| Example 4 | 48.71 | 31.52 | 58.47 | bright orange |
| Example 5 | 51.65 | 49.73 | 43.40 | bright orange red |
| Example 6 | 71.61 | 16.62 | 65.84 | gold-yellow |
| Example 7 | 53.06 | 46.77 | 45.80 | orange-red |
| Example 8 | 47.04 | 42.75 | 9.70 | red-violet |
| Example 9 | 34.48 | 21.39 | 16.72 | brown |
| Example 10 | 33.04 | 22.09 | 16.34 | Bordeaux red |
| Example 11 | 35.60 | 10.28 | 21.48 | chestnut-brown |
| Example 12 | 55.27 | 47.39 | 63.62 | brilliant orange |

Examples 14 to 18

Hair Colorant

A colorant having the following composition was prepared.

| | |
|---|---|
| 10.00 g | of ethanol |
| 1.00 g | of hydroxyethylcellulose |
| 0.29 g | of dye as per Example 1 |
| X g | of direct dye as per Table 2 |
| to 100.00 g | water, demineralized |

The colorant was applied to bleached hair and after an exposure time of 20 min at 40° C. it was rinsed out with water. The hair was then dried.

TABLE 2

| Example No. | Direct Dye | Color |
|---|---|---|
| 14 | 0.25 g of Basic Yellow 57 | bright orange |
| 15 | 0.18 g of Basic Red 76 | orange |
| 16 | 0.35 g of Basic Brown 17 | red-brown |
| 17 | 0.42 g of Basic Blue 99 | eggplant colors |
| 18 | 0.23 g of Basic Yellow 57 | anthracite |
| | 0.31 g of Basic Brown 17 | |
| | 0.28 g of Basic Blue 99 | |

The indicated L*a*b* color values were obtained with a Chromameter II color-measuring instrument supplied by Minolta. Here the L* value stands for brightness (namely the lower the L* value the higher is the color intensity), whereas the a* value is a measure of the red content of the color (namely the higher the a* value the higher is the red content) and the b* value is a measure of the blue content of the color (namely the more negative the b* value, the higher is the blue content).

Unless otherwise indicated, all percentages are by weight.

What is claimed is:

1. An agent for coloring keratin fibers comprising at least one cationic naphthyldiazo dye of general formula (I) and at least one other dye besides the dye of general formula (I),

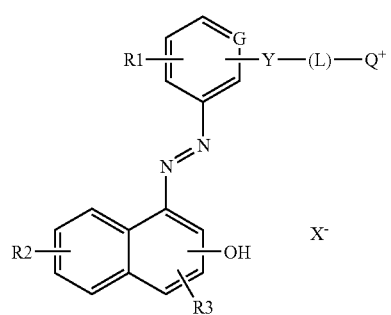

(I)

wherein
R1 stands for a hydrogen atom, halogen atom, straight-chain or branched $(C_1-C_4)$-alkyl group, straight-chain or branched $(C_1-C_4)$-alkoxy group, phenyl group or $(C_2-C_4)$-hydroxyalkyl group;
R2 and R3 can be equal or different and independently of each other stand for a hydrogen atom, hydroxyl group, amino group, acetylamino group, $(C_1-C_6)$-alkoxy group, $(C_2-C_4)$-hydroxyalkoxy group, $(C_3-C_6)$-di- or polyhydroxyalkoxy group, —COOR group, —NRR' group or —CONRR' group, wherein R and R' can be equal or different and stand for a hydrogen atom, a straight-chain or branched $(C_1-C_6)$-alkyl group or a hydroxyethyl group, or R and R' together with the nitrogen atom to which they are attached form a heterocycle with at least four ring members optionally containing other heteroatoms and R and R' and the afore-described heterocycle possibly being substituted with an alkyl group, alkoxy group, hydroxyalkyl group or aminoalkyl group;
G stands for a nitrogen atom or a methine group (CH);
Y stands for an oxygen atom, or an N—$(C_1-C_4)$-alkyl group;
L represents a bridging group and stands for a straight-chain or branched $(C_1-C_{14})$-alkylene group which optionally can be interrupted by one or more heteroatoms, the bridging group optionally being substituted with one or more hydroxyl groups, monohydroxy-$(C_2-C_6)$-alkyl groups, polyhydroxy-$(C_2-C_6)$-alkyl groups or $(C_1-C_6)$-alkoxy groups;
$Q^+$ stands for a saturated cationic group of formula (II) or an unsaturated cationic group of formulas (III) to (V)

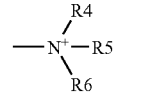

(II)

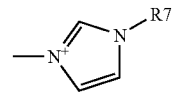

(III)

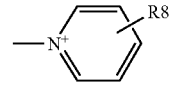

(IV)

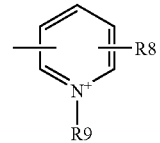

(V)

wherein
R4 to R6 can be equal or different and independently of each other denote a straight-chain or branched $(C_1-C_6)$-alkyl group, $(C_2-C_4)$-hydroxyalkyl group, $(C_3-C_6)$-dihydroxyalkyl group, $(C_3-C_6)$-polyhydroxyalkyl group or $(C_1-C_6)$-alkoxy-$(C_1-C_4)$-alkyl group, or two of the R4 to R6 groups, together with the nitrogen atom to which they are attached, form a five-membered or six-membered heterocycle optionally interrupted by one or more heteroatoms such as an oxygen atom, sulfur atom or nitrogen atom and optionally bearing other substituents, for example a halogen atom, hydroxyl group, amino group, straight-chain or branched $(C_1-C_6)$-alkyl group, $(C_1-C_6)$-alkoxy group, $(C_1-C_6)$-alkoxy-$(C_1-C_4)$-alkyl group or hydroxyethyl group;
R7 stands for a straight-chain or branched $(C_1-C_8)$-alkyl group, allyl group, vinyl group, hydroxyethyl group or benzyl group;
R8 stands for a hydrogen atom, straight-chain or branched $(C_1-C_9)$-alkyl group, amino group, di-$(C_1-C_6)$-alkylamino group or pyrrolidino group;

R9 stands for a straight-chain or branched ($C_1$-$C_8$)-alkyl group, allyl group, vinyl group, hydroxyethyl group, dihydroxypropyl group or benzyl group, and $X^-$ stands for an anion.

2. The agent as defined in claim 1, wherein the dye of formula (I) is selected from dyes wherein R1 stands for a hydrogen atom, a chlorine atom or a methyl group, R2 and R3 are equal or different and independently of each other stand for hydrogen, a hydroxyl group, methoxy group, —NRR' group or —CONRR' group wherein R and R' can be equal or different and stand for a hydrogen atom, a methyl group or a hydroxyethyl group, or R and R' together with the nitrogen atom to which they are attached form a heterocycle with five or six ring members;

G stands for a nitrogen atom or a methine group (CH);

Y stands for oxygen or an N-methyl group;

L stands for a straight-chain ($C_2$-$C_4$)-bridging group;

$Q^+$ stands for a saturated cationic group of formula (II) or an unsaturated cationic group of formulas (III) to (V), the R4 to R6 groups possibly being equal or different and independently of each other denote a straight-chain ($C_1$-$C_3$)-alkyl group, a hydroxyethyl group or a methoxyethyl group, or two of the R4 to R6 groups together with the nitrogen atom to which they are attached form a five-membered or six-membered heterocycle;

R7 stands for a methyl group or hydroxyethyl group;

R8 stands for a hydrogen atom, methyl group, dimethylamino group or pyrrolidino group;

R9 stands for a methyl group, ethyl group or hydroxyethyl group, and $X^-$ stands for a chloride anion, bromide anion or methylsulfate anion.

3. The agent as defined in claim 1, wherein the dye of general formula (I) is selected from among 2-{2-[(2-hydroxy-1-naphthyl)diazenyl]phenoxy}-N,N,N-trimethylethanaminium methylsulfate, 2-{2-[(4-hydroxy-1-naphthyl)diazenyl]phenoxy}-N,N,N-trimethylethanaminium chloride, 2-(2-{2-[(2-hydroxy-1-naphthyl)diazenyl]-phenoxy}ethyl)-1-methylpyridinium methylsulfate, 2-{2-[(2,7-dihydroxy-1-naphthyl)-diazenyl]phenoxy}-N,N,N-trimethylethanaminium chloride, 4-(2-{2-[(2-hydroxy-1-naphthyl)-diazenyl]phenoxy}ethyl)-4-methylmorpholin-4-ium chloride, 2-[(2-{[2-hydroxy-7-(methyloxy)-1-nanhthalenyl]diazenyl}phenyl)oxy]-N,N,N-trimethylethanaminium chloride, 2-[{4-[(2-hydroxy-1-naphthalenyl)diazenyl]phenyl}(methyl)amino]-N,N,N-trimethylethanaminium methylsulfate, 2-[{2-[(2-hydroxy-1-naphthalen-yl)diazenyl]phenyl}(methyl)amino-N,N,N-trimethylethanaminium methylsulfate, 2-[{2-(4-hydroxy-1-naphthalenyl)diazenyl]phenyl}(methyl)amino]-N, N, N-trimethylethanaminium methylsulfate, 2-({5-[(2-hydroxy-1-naphthyl)diazenyl-2-pyridinyl}-oxy)-N,N,N-trimethylethanaminium chloride, 2-({3-[(2-hydroxy-1-naphthyl)diazenyl]-2-pyridinyl}oxy)-N,N,N-trimethylethanaminium chloride, 2-({3-[(4-hydroxy-1-naphthyl)diazenyl]-2-pyridinyl}oxy)-N,N,N-trimethylethanaminium chloride, 2-{3-[(2-hydroxy-1-naphthyl)diazenyl]phenoxy}-N,N,N-trimethylethanaminium chloride, 3-(2-{2-[(2-hydroxy-1-naphthyl)diazenyl]phenoxy}ethyl)-1-methyl-1H-imidazol-3-ium chloride, 2-({2-[(2,4-dihydroxy-1-naphthalenyl)diazenyl]phenyl}oxy)-N,N,N-trimethylethanaminium chloride and 2-{[2-({2-hydroxy-3-[(phenylamino)carbonyl]-1-naphthalenyl}diazenyl)phenyl]oxy}-N,N,N-trimethylethanaminium chloride.

4. The agent as defined in claim 1, wherein the agent contains the dye of formula (I) in a total amount from 0.01 to 10 weight percent.

5. The agent as defined in claim 1, wherein the other dye is selected from among 3-[(4,5-dihydro-3-methyl-5-keto-1-phenyl-1H-pyrazol-4-yl)-azo]-N,N,N-trimethylbenzenaminium chloride, 3[(3-methyl-5-hydroxy-1-phenyl-1H-pyrazol-4-yl)azo]trimethylammoniobenzene chloride, 8[(4-aminophenyl)azo]-7-hydroxy-N,N,N-trimethyl-2-naphthalenaminium chloride, 8-[(4-amino-3-nitrophenyl)-azo]-7-hydroxy-N,N,N-trimethyl-2-naphthalenaminium chloride, 8-[(4-amino-2-nitrophenyl)azo]-7-hydroxy-N,N,N-trimethyl-2-naphthalenaminium chloride, 7-hydroxy-N,N,N-trimethyl-8-{[2-(methyloxy)phenyl]azo}-2-naphthalenaminium chloride, 3-[(4-amino-6-bromo-5,8-dihydro-1-hydroxy-8-imino-5-keto-2-naphthalenyl)-amino]-N,N,N-trimethylbenzenammonium chloride and N,N-dimethyl-3-{[4-(methyl-amino)-9,10-diketo-9,10-dihydro-1-anthracenyl]amino}-N-propyl-1-propanaminium bromide.

6. The agent as defined in claim 1, wherein the agent is a hair colorant.

7. An agent for coloring keratin fibers that is in the form of a tinting fixative or dye fixative, comprising at least one cationic naphthyldiazo dye of general formula (I) and at least one polymer selected from the group consisting of natural polymers, synthetic polymers, and modified polymers of natural origin,

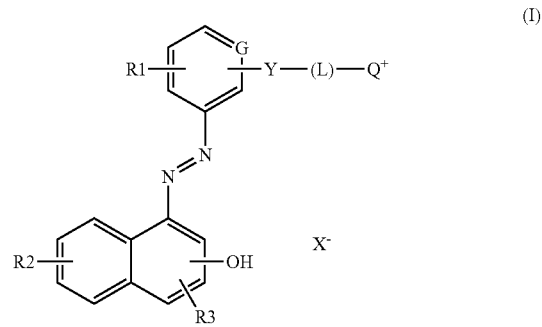

(I)

wherein

R1 stands for a hydrogen atom, halogen atom, straight-chain or branched ($C_1$-$C_4$)-alkyl group, straight-chain or branched ($C_1$-$C_4$)-alkoxy group, phenyl group or ($C_2$-$C_4$)-hydroxyalkyl group;

R2 and R3 can be equal or different and independently of each other stand for a hydrogen atom, hydroxyl group, amino group, acetylamino group, ($C_1$-$C_6$)-alkoxy group, ($C_2$-$C_4$)-hydroxyalkoxy group, ($C_3$-$C_6$)-di- or polyhydroxyalkoxy group, —COOR group, —NRR' group or —CONRR' group, wherein R and R' can be equal or different and stand for a hydrogen atom, a straight-chain or branched ($C_1$-$C_6$)-alkyl group or a hydroxyethyl group, or R and R' together with the nitrogen atom to which they are attached form a heterocycle with at least four ring members optionally containing other heteroatoms and R and R' and the afore-described heterocycle possibly being substituted with an alkyl group, alkoxy group, hydroxyalkyl group or aminoalkyl group;

G stands for a nitrogen atom or a methine group (CH);

Y stands for an oxygen atom, or an N—($C_1$-$C_4$)-alkyl group;

L represents a bridging group and stands for a straight-chain or branched ($C_1$-$C_{14}$)-alkylene group which optionally can be interrupted by one or more heteroatoms, the bridging group optionally being substituted with one or more hydroxyl groups, monohydroxy-($C_2$-$C_6$)-alkyl groups, polyhydroxy-($C_2$-$C_6$)-alkyl groups or ($C_1$-$C_6$)-alkoxy groups;

$Q^+$ stands for a saturated cationic group of formula (II) or an unsaturated cationic group of formulas (III) to (V)

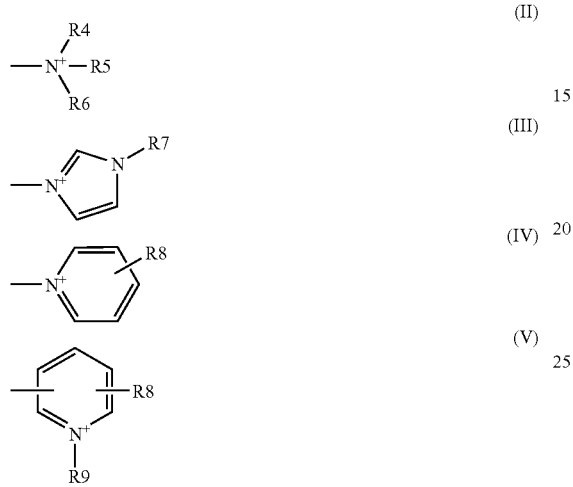

wherein

R4 to R6 can be equal or different and independently of each other denote a straight-chain or branched ($C_1$-$C_6$)-alkyl group, ($C_2$-$C_4$)-hydroxyalkyl group, ($C_3$-$C_6$)-dihydroxyalkyl group, ($C_3$-$C_6$)-polyhydroxyalkyl group or ($C_1$-$C_6$)-alkoxy-($C_1$-$C_4$)-alkyl group, or two of the R4 to R6 groups, together with the nitrogen atom to which they are attached, form a five-membered or six-membered heterocycle optionally interrupted by one or more heteroatoms such as an oxygen atom, sulfur atom or nitrogen atom and optionally bearing other substituents, for example a halogen atom, hydroxyl group, amino group, straight-chain or branched ($C_1$-$C_6$)-alkyl group, ($C_1$-$C_6$)-alkoxy group, ($C_1$-$C_6$)-alkoxy-($C_1$-$C_4$)-alkyl group or hydroxyethyl group;

R7 stands for a straight-chain or branched ($C_1$-$C_6$)-alkyl group, allyl group, vinyl group, hydroxyethyl group or benzyl group;

R8 stands for a hydrogen atom, straight-chain or branched ($C_1$-$C_9$)-alkyl group, amino group, di-($C_1$-$C_6$)-alkylamino group or pyrrolidino group;

R9 stands for a straight-chain or branched ($C_1$-$C_8$)-alkyl group, allyl group, vinyl group, hydroxyethyl group, dihydroxypropyl group or benzyl group, and $X^-$ stands for an anion.

8. The agent as defined in claim 7, wherein the agent contains the dye of formula (I) in a total amount from 0.01 to 10 weight percent.

9. The agent as defined in claim 7, wherein the dye of formula (I) is selected from dyes wherein R1 stands for a hydrogen atom, a chlorine atom or a methyl group, R2 and R3 are equal or different and independently of each other stand for hydrogen, a hydroxyl group, methoxy group, —NRR' group or —CONRR' group wherein R and R' can be equal or different and stand for a hydrogen atom, a methyl group or a hydroxyethyl group, or R and R' together with the nitrogen atom to which they are attached form a heterocycle with five or six ring members;

G stands for a nitrogen atom or a methine group (CH);

Y stands for oxygen or an N-methyl group;

L stands for a straight-chain ($C_2$-$C_4$)-bridging group;

$Q^+$ stands for a saturated cationic group of formula (II) or an unsaturated cationic group of formulas (III) to (V), the R4 to R6 groups possibly being equal or different and independently of each other denote a straight-chain ($C_1$-$C_3$)-alkyl group, a hydroxyethyl group or a methoxyethyl group, or two of the R4 to R6 groups together with the nitrogen atom to which they are attached form a five-membered or six-membered heterocycle;

R7 stands for a methyl group or hydroxyethyl group;

R8 stands for a hydrogen atom, methyl group, dimethylamino group or pyrrolidino group;

R9 stands for a methyl group, ethyl group or hydroxyethyl group, and $X^-$ stands for a chloride anion, bromide anion or methylsulfate anion.

10. The agent as defined in claim 7, wherein the dye of general formula (I) is selected from among 2-{2-[(2-hydroxy-1-naphthyl)diazenyl]phenoxy}-N,N,N-trimethylethanaminium methylsulfate, 2-{2-[(4-hydroxy-1-naphthyl)diazenyl]phenoxy}-N,N,N-trimethylethanaminium chloride, 2-(2-{2-[(2-hydroxy-1-naphthyl)diazenyl]-phenoxy}ethyl)-1-methylpyridinium methylsulfate, 2-{2-[(2,7-dihydroxy-1-naphthyl)-diazenyl]phenoxy}-N,N,N-trimethylethanaminium chloride, 4-(2-{2-[(2-hydroxy-1-naphthyl)-diazenyl]phenoxy}ethyl)-4-methylmorpholin-4-ium chloride, 2-[(2-{[2-hydroxy-7-(methyloxy)-1-naphthalenyl]diazenyl}phenyl)oxy]-N,N,N-trimethylethanaminium chloride, 2-[{4-[(2-hydroxy-1-naphthalenyl)diazenyl]phenyl}(methyl)amino]-N,N,N-trimethylethanaminium methylsulfate, 2-[{2-[(2-hydroxy-1-naphthalen-yl)diazenyl]phenyl}(methyl)amino-N,N,N-trimethylethanaminium methylsulfate, 2-[{2-(4-hydroxy-1-naphthalenyl)diazenyl]phenyl}(methyl)amino]-N,N,N-trimethylethanaminium methylsulfate, 2-({5-[(2-hydroxy-1-naphthyl)diazenyl-2-pyridinyl}-oxy)-N,N,N-trimethylethanaminium chloride, 2-({3-[(2-hydroxy-1-naphthyl)diazenyl]-2-pyridinyl}oxy)-N,N,N-trimethylethanaminium chloride, 2-({3-[(4-hydroxy-1-naphthyl)diazenyl]-2-pyridinyl}oxy)-N,N,N-trimethylethanaminium chloride, 2-{3-[(2-hydroxy-1-naphthyl)diazenyl]phenoxy}-N,N,N-trimethylethanaminium chloride, 3-(2-{2-[(2-hydroxy-1-naphthyl)diazenyl]phenoxy}ethyl)-1-methyl-1H-imidazol-3-ium chloride, 2-({2-[(2,4-dihydroxy-1-naphthalenyl)diazenyl]phenyl}oxy)-N,N,N-trimethylethanaminium chloride and 2-{[2-({2-hydroxy-3-[(phenylamino)carbonyl]-1-naphthalenyl}diazenyl)phenyl]oxy}-N,N,N-trimethylethanaminium chloride.

11. The agent as defined in claim 7, wherein the agent is a hair colorant.

* * * * *